United States Patent
DiFoggio

(10) Patent No.: US 7,969,571 B2
(45) Date of Patent: Jun. 28, 2011

(54) EVANESCENT WAVE DOWNHOLE FIBER OPTIC SPECTROMETER

(75) Inventor: Rocco DiFoggio, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 185 days.

(21) Appl. No.: 12/354,117

(22) Filed: Jan. 15, 2009

(65) Prior Publication Data

US 2010/0177310 A1 Jul. 15, 2010

(51) Int. Cl.
*G01J 3/28* (2006.01)
(52) U.S. Cl. ............................ 356/326; 250/269.1
(58) Field of Classification Search .............. 356/326, 356/328; 250/269.1, 269.2
See application file for complete search history.

(56) References Cited

U.S. PATENT DOCUMENTS

| | | | |
|---|---|---|---|
| 4,437,761 A | 3/1984 | Kroger et al. | |
| 4,699,511 A | 10/1987 | Seaver | |
| 4,781,458 A | 11/1988 | Angel et al. | |
| 4,844,608 A | 7/1989 | Smith | |
| 4,859,844 A | 8/1989 | Herman et al. | |
| 4,994,671 A | 2/1991 | Safinya et al. | |
| 5,005,005 A | 4/1991 | Brossia et al. | |
| 5,168,156 A * | 12/1992 | Fischer et al. | 250/227.21 |
| 5,303,775 A | 4/1994 | Michaels et al. | |
| 5,585,634 A * | 12/1996 | Stevenson et al. | 250/339.11 |
| 5,663,559 A | 9/1997 | Auzerais et al. | |
| 5,663,790 A | 9/1997 | Ekstrom et al. | |
| 5,831,743 A | 11/1998 | Ramos et al. | |
| 6,184,980 B1 | 2/2001 | Brown et al. | |
| 6,223,822 B1 | 5/2001 | Jones | |
| 6,233,746 B1 | 5/2001 | Skinner | |
| 6,343,507 B1 | 2/2002 | Felling et al. | |
| 6,388,251 B1 | 5/2002 | Papanyan | |
| 6,507,401 B1 | 1/2003 | Turner et al. | |
| 6,678,050 B2 | 1/2004 | Pope et al. | |
| 6,683,681 B2 | 1/2004 | Difoggio et al. | |
| 6,975,388 B2 | 12/2005 | Frot | |
| 6,997,055 B2 | 2/2006 | DiFoggio | |
| 7,016,026 B2 | 3/2006 | DiFoggio et al. | |
| 7,028,543 B2 | 4/2006 | Hardage et al. | |
| 7,099,015 B2 | 8/2006 | Melnyk | |

(Continued)

FOREIGN PATENT DOCUMENTS

JP 08219989 A1 8/1996

OTHER PUBLICATIONS

S.T. Huntington, et al. "Evanescent field characterisation of tapered optical fibre sensors in liquid environments using near field scanning optical microscopy and atomic force microscopy". IEE Proc.-Optoelectron., vol. 146, No. 5, Oct. 1999. pp. 239-243.

(Continued)

*Primary Examiner* — F. L Evans
(74) *Attorney, Agent, or Firm* — Cantor Colburn LLP

(57) ABSTRACT

An apparatus for estimating a property of a fluid downhole, is provided an includes: an optical fiber that receives light emitted from a light source and including an unclad portion adapted for contacting the fluid; a photodetector for receiving optical signals from the portion; and a spectrometer for obtaining an evanescent spectrum of the fluid from the portion. A method and a system are included.

21 Claims, 9 Drawing Sheets

U.S. PATENT DOCUMENTS

| | | |
|---|---|---|
| 7,183,778 B2 | 2/2007 | Homan et al. |
| 7,319,523 B2 | 1/2008 | Chiarello et al. |
| 7,330,262 B2 | 2/2008 | Siepmann et al. |
| 7,418,865 B2 | 9/2008 | Griffiths et al. |
| 7,497,256 B2 | 3/2009 | DiFoggio et al. |
| 7,498,567 B2 | 3/2009 | Brady |
| 2003/0193662 A1 | 10/2003 | DiFfoggio et al. |
| 2003/0205083 A1 | 11/2003 | Tubel et al. |
| 2004/0065439 A1 | 4/2004 | Tubel et al. |
| 2006/0175547 A1 | 8/2006 | DiFoggio et al. |
| 2007/0068242 A1 | 3/2007 | DiFoggio |
| 2007/0108378 A1 | 5/2007 | Terabayashi et al. |
| 2007/0268479 A1 | 11/2007 | Downey |
| 2008/0043242 A1 | 2/2008 | Emmerson et al. |
| 2008/0165356 A1 | 7/2008 | DiFoggio et al. |

OTHER PUBLICATIONS

Masoud Ghandehari, et al. "An Evanescent-Field Fiber Optic Sensor For PH Monitoring in Civil Infrastructure". 15th ASCE Engineering Mechanics Conference. Jun. 2-5, 2002, Columbia University, New York, NY.

Wenqi Gong, et al. "The influence of dissolved gas on the interactions between surfaces of different hydrophobicity in aqueous media". Part II. A spectroscopic study. Phys. Chem. Chem. Phys., 1999, 1, 2799-2803.

J.-P. Conzen, et al. "Characterization of a Fiber-Optic Evanescent Wave Absorbance Sensor for Nonpolar Organic Compounds". Applied Spectroscopy, vol. 47, No. 6, 1993. pp. 753-754.

Rocco DiFoggio, Fiber Optic Refractometer. U.S. Appl. No. 11/956,945, filed Dec. 14, 2007.

International Search Report and Written Opinion, Mailed Oct. 12, 2009, International Application No. PCT/US2008/086432, International Search Report 5 Pages, Written Opinion 9 Pages.

Notification of Transmittal of the International Search Report and the Written Opinion of the International Searching Authority, or the Declaration; PCT/US2010/021159; Aug. 24, 2010.

* cited by examiner

US 7,969,571 B2

EVANESCENT WAVE DOWNHOLE FIBER OPTIC SPECTROMETER

BACKGROUND OF THE INVENTION

1. Field of the Invention

The present invention generally relates to well bore tools and in particular to apparatus and methods for estimating properties of downhole fluids.

2. Description of the Related Art

Oil and gas wells have been drilled at depths ranging from a few thousand feet to as deep as five miles. A large portion of the current drilling activity involves directional drilling that includes drilling boreholes deviated from vertical by a few degrees up to horizontal to increase the hydrocarbon production from earth subterranean formations.

Information about the subterranean formations traversed by the borehole may be obtained by any number of techniques. Some techniques used to obtain formation information include obtaining one or more core samples of the subterranean formations and obtaining one or more fluid samples produced from the subterranean formations. These samplings are collectively referred to herein as formation sampling. Modern fluid sampling includes various downhole tests and sometimes fluid samples are retrieved for surface laboratory testing. However, the high costs associated with oil and gas exploration create a great bias toward improved methods and apparatus for downhole testing.

Thus, what are needed are improved methods and apparatus for downhole testing of fluids. Preferably, the methods and apparatus provide users with capabilities to rapidly identify constituents of a fluid sample.

SUMMARY OF THE INVENTION

An embodiment of the invention includes an apparatus for estimating a property of a fluid downhole, the apparatus including: an optical fiber that receives light emitted from a light source and including an unclad portion adapted for contacting the fluid; a photodetector for receiving optical signals from the portion; and a spectrometer for obtaining an evanescent spectrum of the fluid from the portion.

Another embodiment of the invention includes a method for estimating a property of a fluid downhole, the method including: selecting a downhole spectrometer including an optical fiber with at least an unclad portion; at least partially contacting the portion in the fluid downhole; receiving light emitted from a light source through the optical fiber; estimating an evanescent spectrum of the fluid from the received light; and estimating the property from the spectrum.

A further embodiment of the invention includes a system for characterizing a fluid in a downhole environment, the system including: at least one light source for inputting to an optical fiber having an unclad portion adapted for contacting the fluid; a photodetector for receiving optical signals from the portion; a spectrometer for obtaining an evanescent spectrum of the fluid from the portion; and an electronics unit adapted for receiving evanescent spectrum information and characterizing the fluid.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals and wherein.

DESCRIPTION OF THE INVENTION

Disclosed herein are methods and apparatus for at least one of analyzing a downhole fluid and identifying constituents of the fluid by collecting evanescent wave optical absorption spectra. The techniques provided make use of an optical fiber dipped into or at least partially surrounding the fluid. Exemplary optical fibers include those fabricated from silicon, germanium, and sapphire. The techniques are particularly well suited for mid-infrared spectroscopy and may be used to estimate things such as the percentage of oil based mud contamination, as well as concentrations of hydrogen sulfide ($H_2S$), carbon dioxide, ($CO_2$) as well as concentrations of methane, ethane, propane, and butane.

Figure 1:
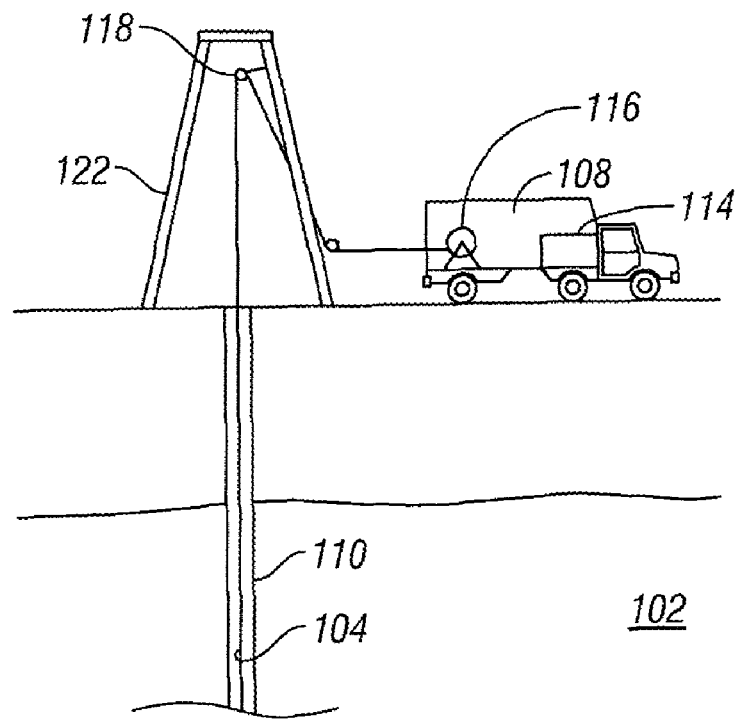
FIG. 1 depicts aspects of a wireline system for performing logging in a borehole.
Figure 1:
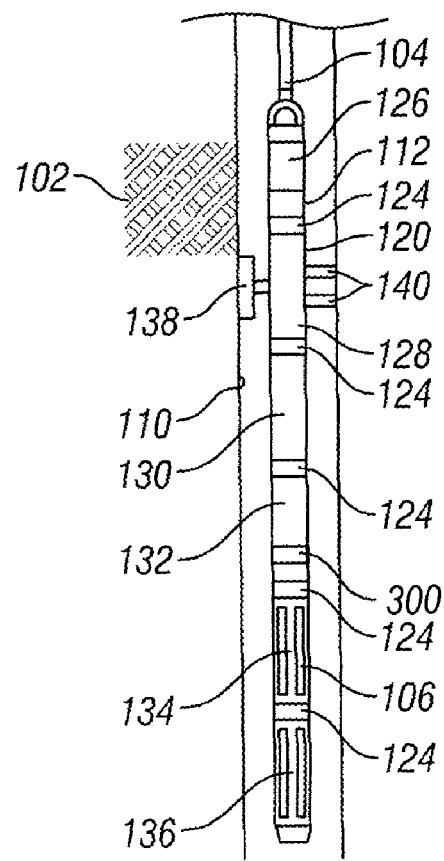

Now for context, consider an exemplary apparatus for oil and gas exploration. FIG. 1 schematically illustrates aspects of a wireline apparatus used for oil and gas exploration. In the example shown, a wellbore 110 or borehole 110 traverses sub-surface materials that may include several subterranean formations 102. The borehole 110 may be filled or at least partially filled with a fluid mixture of including various gases, water, drilling fluid, and formation fluids that are indigenous to the subterranean formations penetrated by the borehole 110. Such fluid mixtures are referred herein to as "wellbore fluids" or "borehole fluids." The terms "connate fluid" and "natural fluid," as used herein, refer to fluids naturally existing in or extracted from the subterranean formations 102 and exclusive of any substantial mixture or contamination by fluids not naturally present in the formation, such as drilling fluid.

In this non-limiting example, a formation evaluation tool 120 is conveyed in the well borehole 110 using a wireline 104. Wire line deployment and retrieval may be performed by a powered winch carried by a service truck 108, for example. The wireline 104 may be an armored cable that carries data and power conductors for providing power to the formation evaluation tool 120 and to provide two-way data communication between a tool processor 112 and a controller 114 that may be carried by the service truck 108. Generally, the wireline 104 is carried from a spool 116 over a pulley 118 supported by a derrick 122. The spool 116 may be carried by the truck 108 as shown for on-land operations, by an offshore rig for underwater operations or by any other suitable mobile or fixed supporting structure. The controller 114 may include a processor, such as within a computer or a microprocessor, data storage devices, such as solid state memory and magnetic tapes, peripherals, such as data input devices and display devices, and other circuitry for controlling and processing data received from the formation evaluation tool 120. The surface controller 114 may further include one or more computer programs embedded in a computer-readable medium accessible to the processor in the controller 114 for executing instructions contained in the computer programs to perform the various methods and functions associated with the processing of the data from the formation evaluation tool 120. It may also be useful in production logging to identify the fluid phases flowing into the wellbore and to identify which phases (gas, water, oil) are being produced from a particular perforation in the casing.

A lower portion of the formation evaluation tool 120 may include an assembly of several tool segments that are joined end-to-end by threaded sleeves or mutual compression unions 124. An assembly of tool segments appropriate for the present invention may include a power unit 126 that may include one or more of a hydraulic power unit, an electrical power unit or an electromechanical power unit. In the example shown, a formation fluid extractor 128 is coupled to the formation evaluation tool 120 below the power unit 126. A large displacement volume motor/pump unit 130 may be provided below the formation fluid extractor 128 for line purging. A similar motor/pump unit 132 having a smaller displacement volume may be included in the tool in a suitable location, such as below the large volume pump, for quantitatively monitoring fluid received by the formation evaluation tool 120. One or more sample tank magazine sections 134 may be included for retaining fluid samples from the small volume pump 132. Each magazine section 134 may have several fluid sample tanks 136. In several embodiments to be described in further detail later, the formation evaluation tool 120 includes a downhole spectrometer 300. The downhole spectrometer 300 may be used in either the while-drilling embodiments or in the wireline embodiments.

The formation fluid extractor 128 generally includes an extensible suction probe 138 that is opposed by bore wall feet 140. Both, the suction probe 138 and the opposing feet 140 may be hydraulically or electro-mechanically extendable to firmly engage the well borehole wall.

Figure 2:
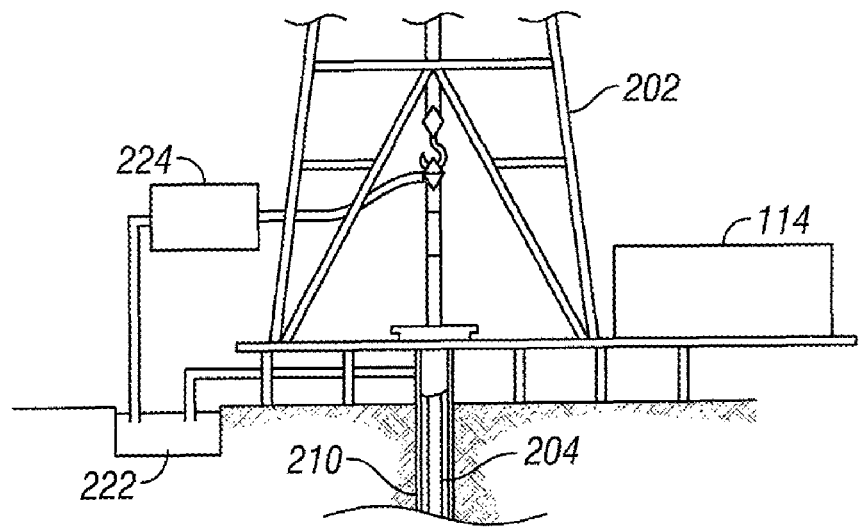
FIG. 2 depicts aspects of a system for performing logging-while-drilling.
Figure 2:
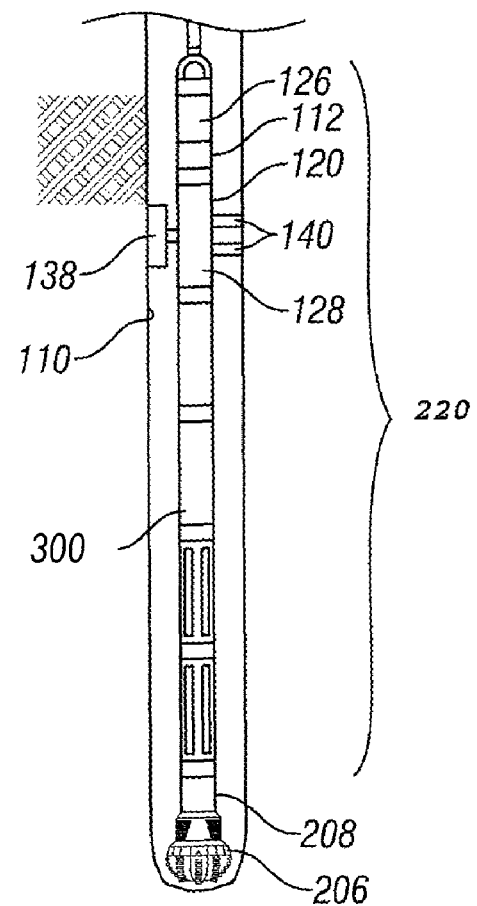

FIG. 2 schematically illustrates a non-limiting example of a drilling system 200 in a measurement-while-drilling (MWD) arrangement according to several non-limiting embodiments of the disclosure. A derrick 202 supports a drill string 204, which may be a coiled tube or drill pipe. The drill string 204 may carry a bottom hole assembly (BHA) 220 and a drill bit 206 at a distal end of the drill string 204 for drilling the borehole 110 through the various earth formations and sub-surface materials.

Drilling operations according to several embodiments may include pumping drilling fluid or "mud" from a mud pit 222, and using a circulation system 224, circulating the mud through an inner bore of the drill string 204. The mud exits the drill string 204 at the drill bit 206 and returns to the surface through an annular space between the drill string 204 and inner wall of the borehole 110. The drilling fluid is designed to provide a hydrostatic pressure that is greater than the formation pressure to avoid blowouts. The pressurized drilling fluid may further be used to drive a drilling motor 208 and may provide lubrication to various elements of the drill string 204.

In the non-limiting embodiment of FIG. 2, the BHA 220 includes a formation evaluation tool 120 substantially similar to the formation evaluation tool 120 described above and shown in FIG. 1.

Figure 6:
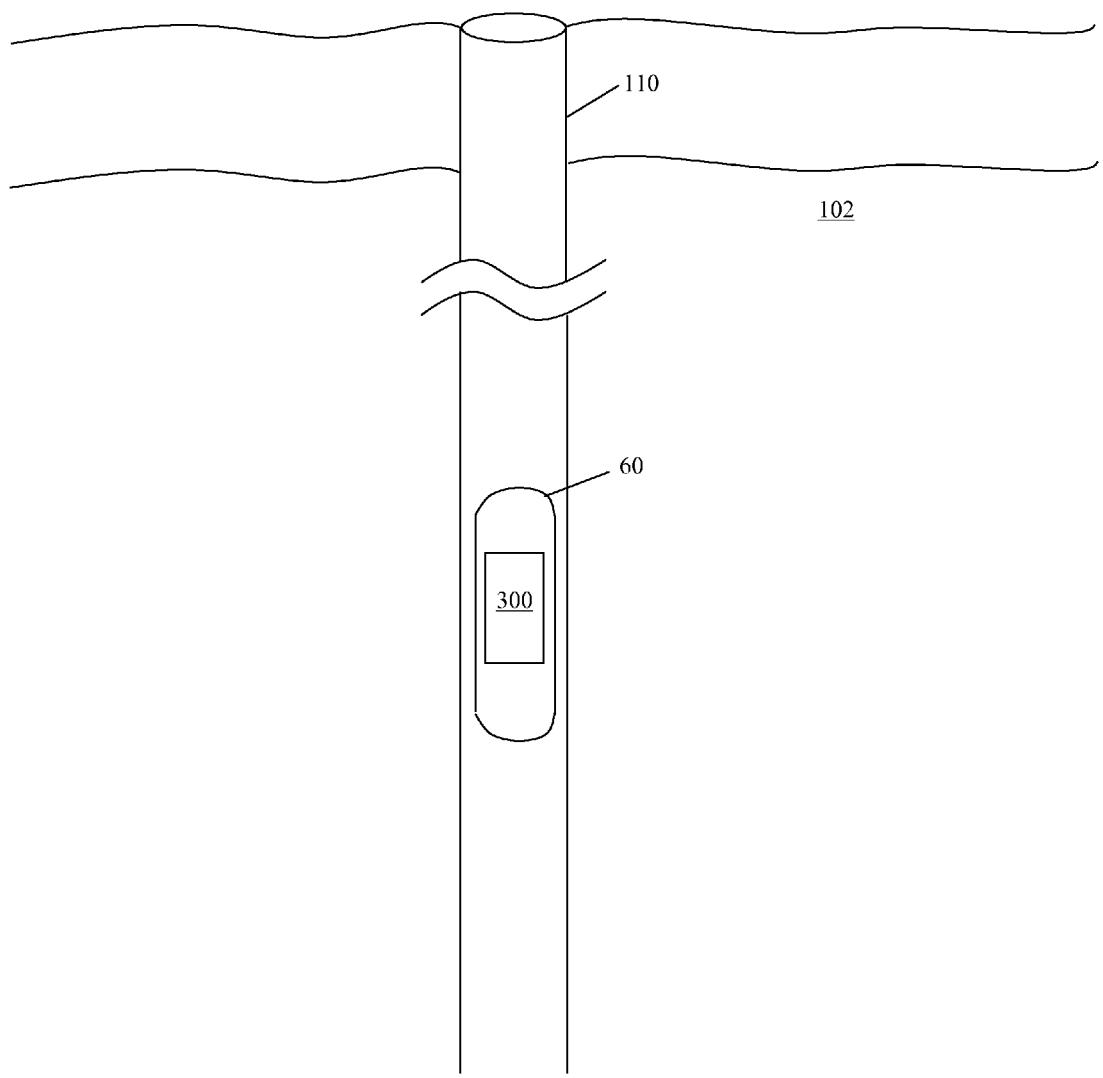
FIG. 6 depicts aspects of a tractor.

The while-drilling formation evaluation tool 120 may carry a fluid extractor 128 including an extendable suction probe 138 and opposing feet 140. In several embodiments to be described in further detail later, the formation evaluation tool 120 includes the downhole spectrometer 300. The downhole spectrometer 300 may be used in either the while-drilling embodiments or in the wireline embodiments. Of course, other embodiments may be realized as well. For example, the downhole spectrometer 300 may be used as a part of a tractor (i.e., a device deployed downhole, independent of a wireline, and generally self-propelled). A general depiction of a tractor 60 disposed in the borehole 110 and having the spectrometer 300 is shown in FIG. 6.

Figure 3:
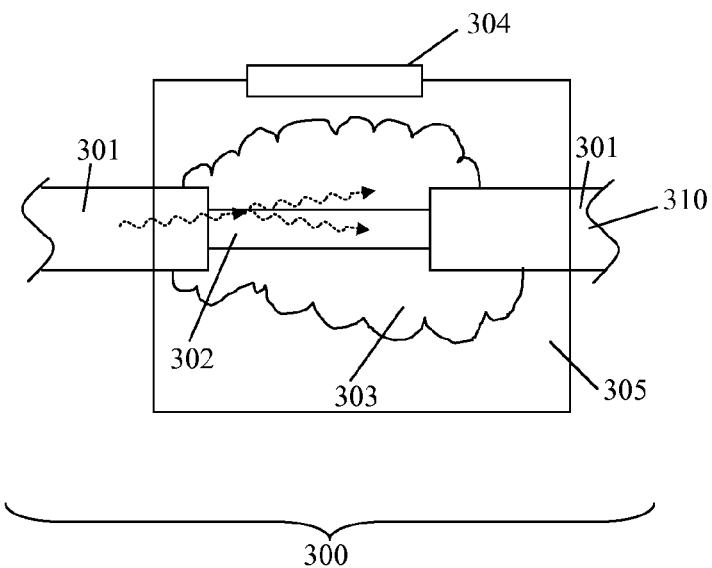
FIG. 3 depicts aspects of a fiber optic spectrometer useful for characterizing petroleum.

Referring to FIG. 3, and with regard to evanescent wave spectroscopy and the downhole spectrometer 300, an illustration is provided for enhanced perspective. In FIG. 3, an optical fiber 310 generally includes a cladding 301 and a core 302. In this example, which depicts some aspects of the downhole spectrometer 300, a portion of the fiber 310 is stripped bare. That is, the core 302 is exposed and without the surrounding cladding 301. This portion of the fiber 310 may be referred to as "unclad." The portion of the core 302 that is exposed is at least partially surrounded by a sample 303, and may be included in or traverse a sample chamber 305 (such as a trough, a cell, a sample line, a volume a sampling area or similar device). It should be recognized that the unclad portion, while it may be within a sample chamber 305, may be in any area or volume where the sample 303 comes into contact within at least some of a surface of the unclad portion. The sample 303 of downhole fluid may be a flowing fluid or a non-flowing fluid. In general, the fluid may be pumped, ported, added, flowed, loaded, let or by any other manner, moved to contact the unclad portion for analysis.

A light beam is provided to an interface of the fiber 310. As the light traverses the exposed portion of the core 302, the light that is incident on the core/sample interface is partially reflected, and partially refracted into the sample 303. This occurs if an angle of incidence is smaller than a critical angle. With an increase in the angle of incidence, the portion of reflected light is increased, and, if the angle of incidence exceeds a critical angle, total internal reflection is realized. The critical angle depends on the refractive indices of the core material, $n_1$, and the sample material, $n_2$. A harmonic wave is referred to as the "evanescent wave." The evanescent wave penetrates into the sample 303 to a penetration depth, $d_p$, and is described by Eq. (1):

$$E = E_0 e^{(-z/d_p)} \quad (1);$$

where z represents a distance normal to the interface between the sample 303 and the core 302, $E_0$ represents amplitude of a wave at z=0. A penetration depth, d, into the sample 303 is given by Eq. (2):

$$d_p = \lambda/(n_1 \cdot 2\pi)(\sin^2\theta - (n_1/n_2)^2)^{0.5} \quad (2);$$

where λ represents a wavelength of light in the core 302 of the fiber 310, $n_1$ represents a refractive index (RI) of the core 302, and $n_2$ represents the refractive index of the sample 303. Accordingly, and as an example, for an input of θ=85 (degrees), λ=2,000 (nm), $n_1$=1.75 and $n_2$=1.5, the penetration depth, $d_p$, is estimated as 92.34 nm.

The fiber optic spectrometer herein includes various adaptations to provide for operation in a downhole environment. For example, some materials used previously for mid-infrared optical fibers (such as silver halides) are not practical for use downhole as such materials are brittle and break easily. Further, such materials have an unacceptably high solubility and reactivity in formation fluids such as brines or crude oils, and that solubility and reactively increases in the high temperatures encountered in the downhole environment.

Accordingly, the teachings herein provide for embodiments of a downhole spectrometer that makes use of, among other things, optical fiber material with a high refractive index, little or no solubility, and little or no reactivity in formation fluids at high temperature, and little absorption over the wavelengths of interest.

Materials selected for the downhole spectrometer 300 generally exhibit a selected group of properties, such as and without limitation, non-stick surfaces, non-corrosive, high refractive index, insolubility and other properties as would be desired downhole. Appropriate materials for the downhole spectrometer 300 generally will not deteriorate at high temperature in the presence of water.

Accordingly, in some embodiments, a metalloid is used for the downhole spectrometer 300. A metalloid behaves like a mirror at shorter wavelengths and like a transparent window at longer wavelengths. The metalloid, in one example, silicon, has an added advantage of being an almost non-reactive and non-stick surface so it is resistant to both corrosion by the fluid and fouling by deposits from the fluid. Germanium is also fairly non-reactive chemically and a suitable material. Silicon and germanium are both semiconductors so they have a bandgap, which is why they operate as a mirror to photons with energy greater than the bandgap and operate as a transparent window to photons with energy less than the bandgap energy. Silicon, for example, changes behavior from that of a mirror to a window at wavelengths longer than about 1,100 nm and germanium changes from a mirror to a window at wavelengths longer than about 1,800 nm.

In order to provide some context for the teachings herein, a review of fundamentals of fiber optics in relation to the downhole spectrometer is now provided. A principle of fiber optics is that light is totally reflected at a core-cladding interface whenever light strikes that interface at a glancing angle that exceeds a critical angle. The core of the fiber must have a higher refractive index than the cladding that surrounds the core for existence of the critical angle. However, even in the case of total internal reflection, there is an evanescent field of the reflected light that exponentially decays beyond the core. This means that a portion of the light slightly penetrates the cladding to a depth this is less than a few wavelengths. If the cladding happens to be so highly absorbing of the wavelengths of light, such that significant light is absorbed within the evanescent penetration depth, d., then one can obtain the attenuated reflectance spectrum of the cladding. If one uses a material exhibiting a sufficiently high refractive index for the core of the fiber, then the formation fluid at least partially surrounding the core is inserted would act as the cladding. In this case, one could obtain an absorption spectrum for the formation fluid using the evanescent signal. The fundamental molecular vibrational bands, which occur in the mid-infrared regions of the spectrum (about 2.5 to 11 microns), are several orders of magnitude more absorbing than the overtone and combination bands that occur in the near-infrared (0.8 to 2.5 microns) region of the spectrum. The effective pathlength for an evanescent wave spectrometer is quite short. It equals the product of the penetration depth of only less than a few microns with the number of internal reflections. Because the measured absorbance is the product of the effective pathlength and absorptivity, it is preferable to make evanescent-wave measurements in the high-absorptivity, mid-infrared region to compensate for the short effective pathlength.

In order to provide a robust downhole spectrometer, the core material of the fiber must have high chemical and thermal resistance to withstand the harsh downhole environment. The core material should also have a refractive index that is higher than typical downhole gas (RI<1.3) brine (RI in the range 1.30-1.33) or crude oil (RI in the range 1.40-1.55). Preferably, it should also have the ability to transmit mid-infrared light. Examples of suitable materials include sapphire (RI=1.75, transmits to wavelengths as long as 5 microns), elemental silicon (RI=3.4, transmits to wavelengths as long 11 microns), elemental germanium (RI=4, transmission to wavelengths as long 20 microns) and other such materials. Elemental silicon and germanium look like shiny metals in the visible region of the electromagnetic spectrum, but become transparent at longer wavelengths (1,100 nm for silicon and 1,800 nm for germanium). The mid-infrared region is of particular interest for use with a downhole spectrometer, and ranges from about 2,500 nm (2.5 microns) to 11,000 nm (11 microns).

Thus, it can be seen that selection of the optical fiber 310 should consider properties of materials in the core 302 as well as properties of the sample 303. Table 1 below provides non-limiting examples of suitable materials for use in the core 302 of the optical fiber 310 in comparison to properties of sample materials.

TABLE 1

Refractive Indices for Downhole Spectrometer, $n_1$, and Sample, $n_2$

| $n_1$ = Core Refractive Index | | $n_2$ = Fluid Refractive Index | |
|---|---|---|---|
| Sapphire ($Al_2O_3$) | 1.75 | Brine | 1.3 to 1.33 |
| Silicon | 3.42 | Crude Oils | 1.4 to 1.55 |
| Germanium | 4.00 | Gas | <1.3 |
| Boron | 3.0 | | |
| Tellurium | 1.7-2.7 | | |
| Diamond film | 2.42 | | |
| Gallium Lanthanum Sulphide | 2.40 | | |
| Rutile ($TiO_2$) | 2.56 | | |
| Yttrium Aluminum Garnet (YAG) | 1.82 | | |

Specific aspects and considerations of various materials are not provided. While it is considered that metalloids are generally appropriate, arsenic, polonium and antimony have not been considered nor evaluated for use in the downhole spectrometer 300 due to toxicity concerns. However, this is not to suggest that these materials would not perform well. Rather, it is considered that there is a probability that such materials might likely work well as being members in the family of metalloids.

With regard to other materials and considerations for construction of the downhole spectrometer 300, thin films of tellurium show favorable properties, such as low band-gap and transparency in the infrared region. Diamond exhibits a transmission range of about 300 nm to 2.5 microns and a refractive index 2.4175@0.589 micron, and is insoluble in water. Germanium, has a transmission range of about 1.8 to 23 micron, a refractive index 4.0026 at 11 micron and is insoluble in water. Gallium Lanthanum Sulphide is a chalcogenide glass and an alternative to toxic arsenic-based glasses, which exhibits a transmission range of about 0.5 to 10 micron, and a refractive index 2.398 at 1.014 micron. Rutile (Titanium dioxide), exhibits a transmission range of about 0.43 to 5.0 microns, a refractive index of 2.555 at 0.69 microns and is insoluble in water. Sapphire exhibits a transmission range of about 0.17 to 5.5 microns and a refractive index of 1.75449. Silicon exhibits a transmission range of about 1.2 to 15 microns, a refractive index of 3.4223 at 5 microns and is insoluble in water. YAG (Yttrium aluminum oxide $Y_3Al_5O_{12}$) exhibits a transmission range of about 0.21 to 5.5 microns, a refractive index of 1.81523 at 1.06 microns, and is insoluble in water.

Figure 7:
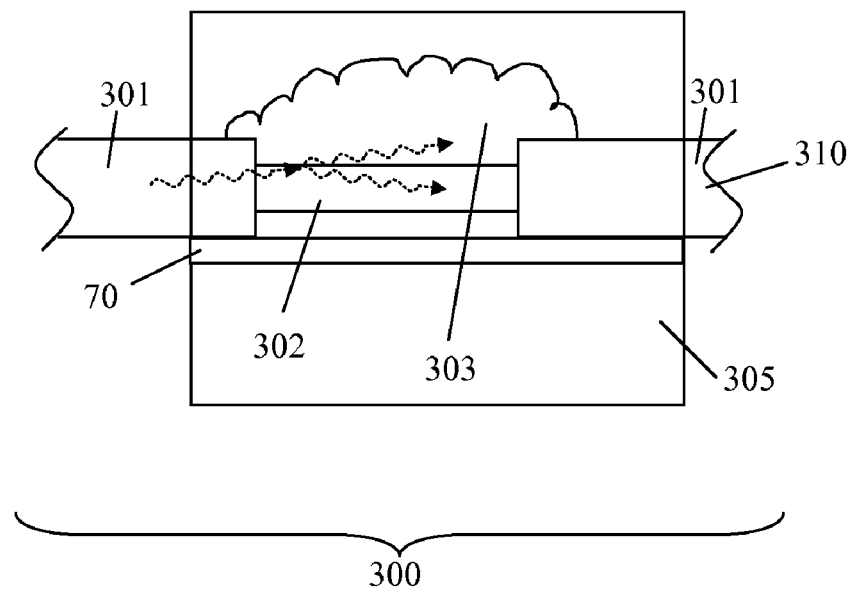
FIG. 7 depicts aspects of an optical fiber attached to a substrate.
Figure 10:
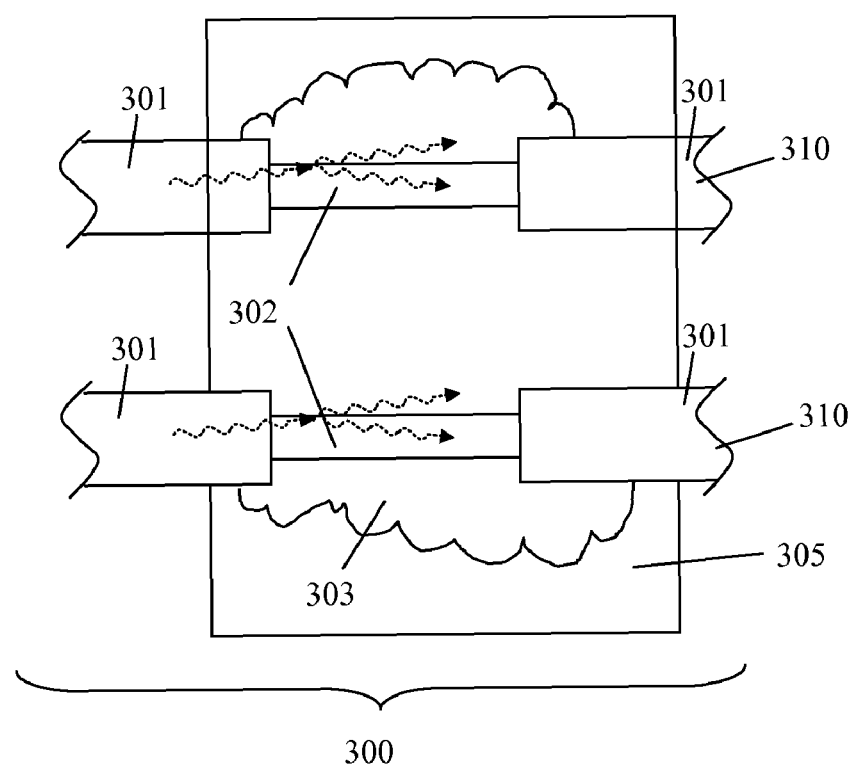
FIG. 10 depicts aspects of the fiber optic spectrometer having a plurality of optical fibers.

The downhole spectrometer 300 may be realized in various forms. In one embodiment, the optical fiber 310 (such as a silicon fiber or a germanium fiber) is attached to a substrate 70 as shown in FIG. 7. The substrate provides mechanical reinforcement that reduces fragility, as embodiments using semi-metals are somewhat brittle. Accordingly, the optical fiber 310 mounted on a substrate generally provides users with a design that is vibration tolerant. Some further embodiments of vibration tolerant designs include mounting on resilient devices, such as springs for motion dampening and the like. In one or more embodiments, the downhole spectrometer 300 includes a plurality of optical fibers 310 as shown in FIG. 10.

Figure 8:
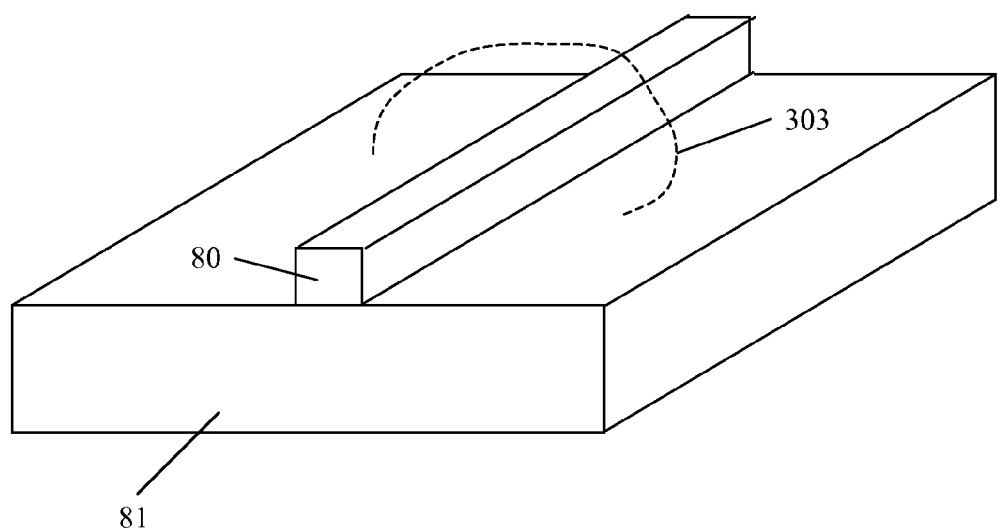
FIG. 8 depicts aspects of a photonic wire waveguide on a substrate.

In some other embodiments, the downhole spectrometer includes a photonic wire (such as a silicon wire) waveguide on a substrate which is very sensitive to trace amounts of sample 303. FIG. 8 illustrates a general depiction of a photonic wire waveguide 80 on a substrate 81. In further embodiments, the downhole spectrometer 300 includes small attenuated reflectance optical windows out of silicon or germanium (for example, windows between about 2 mm and about 3 mm). More specifically, Finite Element Analysis shows that such windows made out of these semi-metals can withstand downhole pressures and temperatures. FIG. 3 illustrates a general depiction of an attenuated reflectance optical window 304 disposed in the downhole spectrometer 300.

Figure 9:
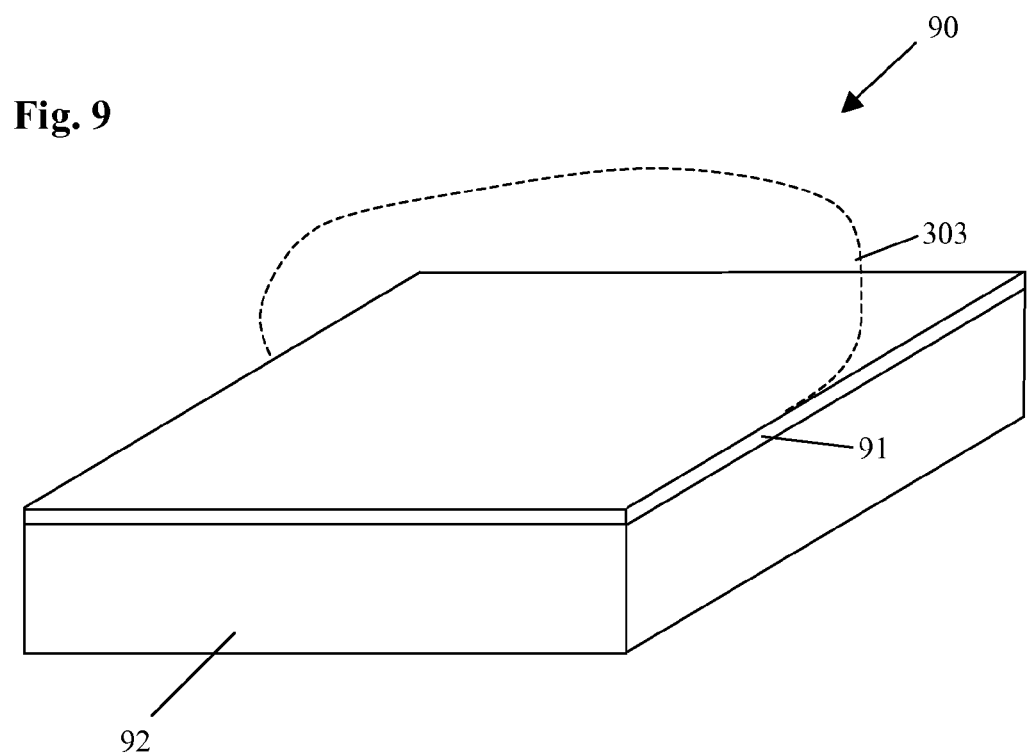
FIG. 9 depicts aspects of a thin film waveguide.

In addition, various other physical forms of fiber optic material may be used. More specifically, it is recognized that certain aspects of the teachings herein are provided in the context of an optical fiber. However, the downhole spectrometer 300, at least in some embodiments, may be realized in other forms, such as a thin film waveguide. That is, in some instances, thin films may provide waveguides of material that might not meet all performance criteria downhole. For example, thin film waveguides can provide robust embodiments of the downhole spectrometer 300 while using materials such as brittle boron, diamond, silicon, germanium, sapphire, etc. In embodiments using thin film waveguides, the material used in the downhole spectrometer can be supported on a rigid substrate and can be prepared by standard wafer processing techniques. These thin films, "optical wires" or "silicon photonics" may act as optical waveguides the same way that a round optical fiber would, even though they have a different cross section, such as a square or a rectangular cross section. Accordingly, as used herein, the terms "fiber optic," "optical fiber," "downhole spectrometer" and other such related terms should be construed to include thin film waveguides of a form useful for performing evanescent spectroscopy downhole. A general depiction of a thin film waveguide 90 having a thin film 91 supported on a substrate 92 is shown in FIG. 9.

Figure 4:
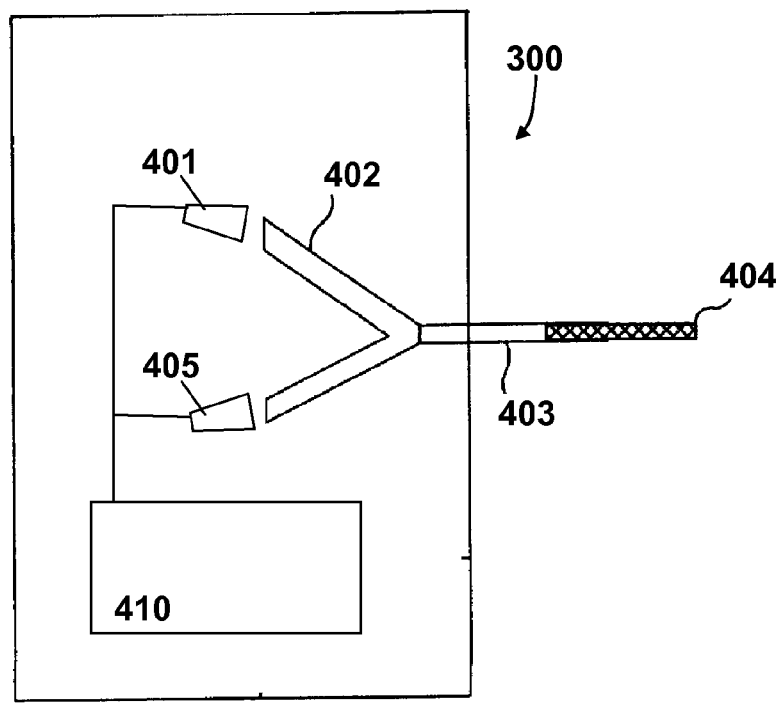
FIG. 4 depicts aspects of another embodiment of the fiber optic spectrometer useful for characterizing petroleum.

Referring now to FIG. 4, aspects of another embodiment of the downhole spectrometer 300 are shown. In this example, the downhole spectrometer 300 includes an infrared light source 401 in optical communication with a waveguide 402 (which may be hollow) for transmitting light into a fiber optic element 403. In some embodiments, at the distal end of the fiber optic element 403 a mirror 404, such as a gold mirror 404 at the tip end of the fiber that may be included and used to reflect the light in the fiber optic element 403. The crude oil or other fluid to be analyzed acts as cladding on the fiber and is denoted by the hatch marks between the labels 403 and 404. The waveguide 402 transmits the reflected light to at least one photodetector 405. The photodetector 405 may include, for example, a plurality of detecting elements for wavelength(s) specific to oil, or other selected downhole fluid(s). Electronics 410 may be included and used to control the light source 401, analyze signals from the photodetector 405 and to transmit signals to remote locations as desired.

The photodetector 405 is generally used to receive light emitted from the light source 401 after the light interacts with the fluid via the return optical fiber 403. In one or more embodiments, the photodetector 405 comprises a single broadband photodetector responsive to light emitted from the light source 401 and/or light reflected at a fluid-metalloid interface. In other non-limiting embodiments, the photodetector 405 includes a dual-layer photodetector responsive to light emitted from the light source 401 and/or light reflected at the fluid-metalloid interface. One suitable embodiment for the photodetector 405 includes a dual-layer photodetector that is a dual-layer Si and InGaAs photodetector. The photodetector 405 provides an output signal indicative of the light received at the photodetector 405 to the electronics unit 42.

In some cases, the photodetector output signal may be an analog electrical signal, so an analog-to-digital converter may be used to convert the photodetector output signal into a digital signal that is received by a downhole controller within the electronics unit 410 or by a surface controller 114. The light emitted from the light source 401 may be modulated by a processor within the same controller that receives the output of the photodetector 405 or by a modulator in a separate controller. In the example shown, one modulator/controller is coupled to the photodetector 405 and a second modulator/controller is coupled to the light source 401. These controllers may be implemented as a single controller without departing from the scope of the disclosure. In other embodiments, the controller or controllers may be located at the surface of the well borehole as described above and show in FIGS. 1 and 2 at 114 using any of several communication methods. Cooling one or more of these downhole components may be accomplished using a cooling device. The cooling device used may be any one or more of a number of devices, examples of which include thermal-electric, thermo-tunneling, sorption cooling, evaporators and a dewar. Cooling is optional where components selected are compatible with the downhole temperature environment.

Cooling may be applied where a component operating temperature is lower than the downhole environment and/or were cooling may enhance performance of the downhole spectrometer 300. In several embodiments, the light source 401 is compatible with the downhole temperature environment and the cooling device is optional. Cooling, in some cases, improves a signal-to-noise ratio of the photodetector 405 and increases laser brightness where the light source 401 includes one or more lasers.

The non-limiting examples of spectrometer tools disclosed herein provide a small, lightweight, fiber-optic downhole spectrometer that has substantially higher resolution than conventional spectrometers. Moreover, the spectrometer 300 may include in-situ calibration capabilities, such as through use of a positionable reference material and a light source generating both short and long wavelengths.

In several embodiments, the light source 401 may include one or more broadband light sources such as an incandescent light source along with an optical filter to provide selected wavelengths, or the light source 401 may include one more light-emitting diodes (LED). The light source may also use one or more laser diodes. In other embodiments, the downhole spectrometer 300 may include one or more light sources 401 that include a combination of light source types. Some embodiments may be used as multi-wavelength implementations. For example, an incandescent light and dual-bandpass filter may be used as a light source 401 to generate two selected wavelengths. Alternatively, dual wavelength diodes or laser diodes may be used. The dual wavelength light may be conveyed via the optical fiber 403 to a silicon or germanium tip immersed in target fluid within a fluid cell. A dual-layer photodetector 405 above may be used to detect light reflected at the fluid interface. In one embodiment, the two wavelengths include a short wavelength light and a long wavelength light, where the short wavelength light is a light having an energy less than the bandgap of the metalloid material and the long wavelength light is a light having an energy greater than the bandgap of the metalloid material.

As one skilled in the art will recognize, a "single wavelength" as discussed herein may actually appear as a band of wavelengths, such as a peak in a spectrum. Accordingly, a plurality of wavelengths may actually be manifested as a plurality of bands of wavelengths such as may be effectively discriminated by associated electronics. Further, use of various types or combinations of optical filters may refine light and wavelength groups as may be used with the downhole spectrometer 300. In some embodiments, the light source 32 may be adjusted so as to multiplex varying wavelengths by time.

The dual wavelength photo detector may provide a short wavelength detector and a long wavelength detector to simultaneously detect the wavelengths reflected at the fluid interface. In some embodiments, when using a fiber having a Si or Ge material and a Si and InGaAs detector, the Si portion of the detector will detect the higher intensity reflections of the short wavelength light while the InGaAs portion of the detector detects lower intensity reflections of the long wavelength light.

With regard to selection of materials, an advantage of a silicon interface is that a silicon interface provides a smooth surface that is resistant to fouling by downhole fluid deposits. Furthermore, silicon acts as a mirror for light wavelengths shorter than about 1,100 nm and is substantially transparent to wavelengths longer than about 1,100 nm. This characteristic is useful in the dual-wavelength embodiments described above. As discussed above, germanium is another exemplary metalloid providing suitable properties for use as the optical fiber.

In some embodiments, at least one of the light source 401, the electronics unit 410 and the photodetector 405 may be maintained remotely. For example, the at least one of the light source 401, the electronics unit 410 and the photodetector 405 may be provided topside. In such embodiments, users and designers are afforded opportunities to employ a greater array of components for performing required tasks. In such embodiments, communication to components of the downhole spectrometer 300 may occur through a variety of devices, including, without limitation, wired pipe, fiber, telemetry and the like. In other embodiments, the at least one of the light source 401, the electronics unit 410 and the photodetector 405 may be included in the downhole spectrometer 300 proximate to the sample chamber 305. In these latter embodiments, the downhole spectrometer 300 may make use of components such as downhole power supplies, cooling units and the like.

In general, the downhole spectrometer 300 provides results on a "real-time" basis. That is, the downhole spectrometer 300 provides results at a rate that is useful to users and operators of downhole equipment during use of such equipment. Generally, the rate is adequate for the users and operators to make meaningful decisions regarding the downhole environment and further downhole sequences.

Figure 5:
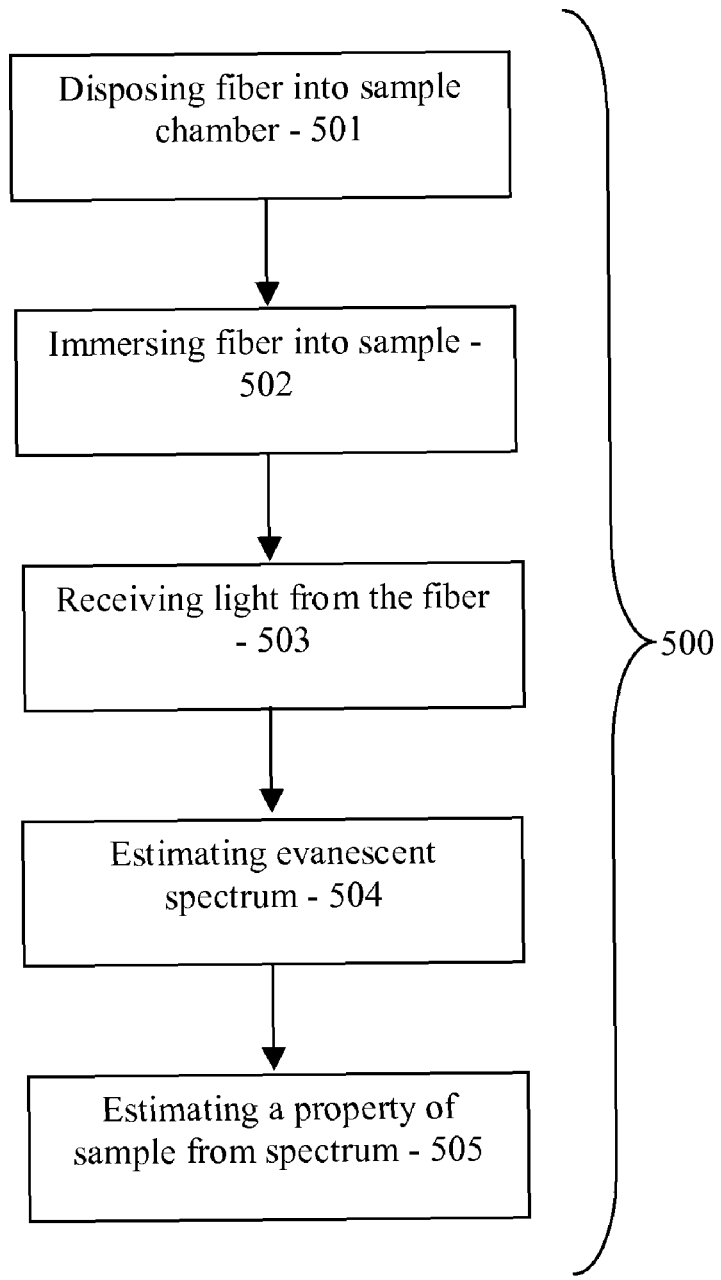
FIG. 5 is a flow chart providing an exemplary method for characterizing fluid(s) with the downhole spectrometer.

Referring now to FIG. 5, there is shown an exemplary method for estimating a property of a fluid downhole. In a first stage 501, the method calls for selecting a downhole spectrometer comprising an optical fiber with at least a portion without a cladding disposed thereon. In a second stage 502, the method calls for at least partially surrounding the portion in the fluid downhole. In a third stage 503, the method calls for receiving light emitted from a light source through the optical fiber. In a fourth stage 504, the method calls for estimating an evanescent spectrum of the fluid from the received light. In a fifth stage 505, the method calls for estimating the property of the sample according to the evanescent spectrum.

Having introduced aspects of the invention, certain advantages of the teachings herein should become apparent. For example, the downhole spectrometer provided herein is generally offers simplified manufacture over prior art designs. More specifically, the use of a single fiber avoids incorporation of optical interface(s) beyond those needed between the light source and the photodetector. Further, use of the single fiber provides for simplified assembly of components. That is, using a fiber further avoids complications realized in the use of components such as reflectance crystals that have attendant geometric requirements. Accordingly, the downhole spectrometer provided herein is generally more robust physically as well as more economic to manufacture or replace.

As provided above, this invention provides for analyzing downhole fluids by collecting evanescent wave optical absorption spectra of the fluid, but by using a silicon, germanium, sapphire or other high temperature and otherwise robust optical fiber dipped into or at least partially surrounded by the sample fluid. This approach is well suited for mid-infrared spectroscopy and determining things such as the percentage of oil based mud contamination, or concentrations of $H_2S$ or $CO_2$ methane, ethane, propane, and butane and other such constituents of petroleum.

In support of the teachings herein, various analysis components may be used, including a digital system and/or an analog system. The system(s) may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a sample line, sample storage, sample chamber, sample exhaust, pump, piston, power supply (e.g., at least one of a generator, a remote supply and a battery), vacuum supply, pressure supply, refrigeration (i.e., cooling) unit or supply, heating component, motive force (such as a translational force, propulsional force or a rotational force), magnet, sensor, controller, optical unit, electrical unit or electromechanical unit may be included in support of the various aspects discussed herein or in support of other functions beyond this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for estimating a property of a fluid downhole, the apparatus comprising:
   a waveguide that receives electromagnetic energy emitted from a source of electromagnetic energy, the waveguide comprising a core portion configured to communicate electromagnetically with the fluid and an unclad portion configured to contact the fluid; and
   a detector configured to receive a resultant signal from the core portion, the resultant signal being used at least in part for estimating the property;
   wherein the waveguide comprises at least one of a thin film waveguide and a photonic wire waveguide.

2. The apparatus as in claim 1, wherein the waveguide comprises one of silicon, germanium and sapphire ($Al_2O_3$), boron, tellurium, diamond, gallium lanthanum sulphide, rutile ($TiO_2$), and yttrium aluminum garnet (YAG).

3. The apparatus as in claim 1, further comprising the source of electromagnetic energy.

4. The apparatus as in claim 3, wherein the source of electromagnetic energy comprises at least one of an incandescent light, a light-emitting-diode, a dual wavelength diode, a laser diode, a single band of wavelengths, a plurality of bands of wavelengths and a filter.

5. The apparatus as in claim 1, where the waveguide is attached to a substrate.

6. The apparatus as in claim 1, further comprising at least one attenuated reflectance optical window in optical communication with the fluid.

7. The apparatus as in claim 1, wherein the waveguide further comprises a plurality of optical fibers for receiving light emitted from the source of electromagnetic energy and having a portion without a cladding disposed thereon.

8. The apparatus as in claim 1, comprising one of a drill string, a wireline instrument and a tractor configured to convey the apparatus downhole.

9. The apparatus as in claim 1, wherein the core portion of the waveguide comprises a refractive index that is greater than a refractive index of the fluid.

10. The apparatus as in claim 1, wherein the waveguide comprises at least one of a low solubility in brine, a low reactivity with the fluid and a high thermal resistance.

11. The apparatus as in claim 1, further comprising a spectrometer configured to obtain an evanescent spectrum from the resultant signal wherein the spectrum is used to estimate the property.

12. The apparatus as in claim 1, wherein the waveguide further comprises an optical fiber.

13. A method for estimating a property of a fluid downhole, the method comprising:
   receiving electromagnetic energy from a source of electromagnetic energy with a waveguide comprising a core portion configured to communicate electromagnetically with the fluid and an unclad portion configured to contact the fluid;
   at least partially contacting the unclad portion in the fluid downhole;
   detecting a resultant signal from the core portion; and
   estimating the property using at least in part the resultant signal.

14. The method as in claim 13, wherein contacting comprises at least one of pumping, porting, adding, flowing, loading, letting and moving the fluid.

15. The method as in claim 13, further comprising estimating an evanescent spectrum of the fluid from the resultant signal wherein the spectrum is used to estimate the property.

16. The method as in claim 15, further comprising classifying the fluid according to the evanescent spectrum.

17. The method as in claim 16, wherein classifying comprises searching a library of sample data.

18. The method as in claim 16, wherein classifying comprises performing a regression of data from the evanescent spectrum.

19. A system for estimating a property of a fluid downhole, the system comprising:
   at least one source of electromagnetic energy for inputting electromagnetic energy to a waveguide comprising a core portion configured to communicate electromagnetically with the fluid and an unclad portion configured to contact the fluid, wherein the waveguide comprises at least one of a thin film waveguide and a photonic wire waveguide;
   a detector configured to receive a resultant signal from the core portion;
   an electronics unit configured to receive the resultant signal and to estimate the property using at least in part the resultant signal.

20. The system as in claim 19, wherein the estimating is performed on a real time basis.

21. The system as in claim 19, further comprising a spectrometer configured to obtain an evanescent spectrum from the resultant signal wherein evanescent spectrum information from the spectrometer is communicated to the electronics unit to estimate the property.

* * * * *